United States Patent [19]
Corella

[11] Patent Number: 5,322,077
[45] Date of Patent: Jun. 21, 1994

[54] DENTAL HYGIENE APPARATUS

[76] Inventor: Arthur P. Corella, 8166 Vanscoy Ave., North Hollywood, Calif. 91602

[21] Appl. No.: 123,689

[22] Filed: Sep. 20, 1993

[51] Int. Cl.$^5$ .................. A61C 15/00; A61B 17/06; A61B 19/02
[52] U.S. Cl. .................. 132/323; 206/63.3; 206/63.5; 206/388
[58] Field of Search .......... 433/141; 132/321, 323, 132/324, 329; 206/63.3, 63.5, 390, 368, 369, 388

[56] References Cited

U.S. PATENT DOCUMENTS

| | | | |
|---|---|---|---|
| 2,921,676 | 1/1960 | Carignan | 206/409 |
| 4,579,221 | 4/1986 | Corella | 206/388 X |
| 4,693,365 | 9/1987 | Corella | 206/388 X |
| 4,712,572 | 12/1987 | Hovel, III | 206/388 X |
| 4,852,728 | 8/1989 | Court | 206/63.5 |
| 4,986,289 | 1/1991 | McWhorter | 206/63.5 X |

Primary Examiner—John G. Weiss
Assistant Examiner—Nicholas D. Lucchesi
Attorney, Agent, or Firm—Donald Diamond

[57] ABSTRACT

A package for storing a plurality of strands of flaccid items, filaments and the like, especially, for the storage of strands of dental floss. First and second ends of the floss are securely sealed within the sealed edge of the package. However, the first and second ends are not permanently sealed within the sealed edges. As a result, when the floss is removed from the sealed package only a small hole, slightly larger than the diameter of the floss, is produced. Consequently, a single piece of floss can be removed from the package without destroying the integrity of the entire package.

20 Claims, 2 Drawing Sheets

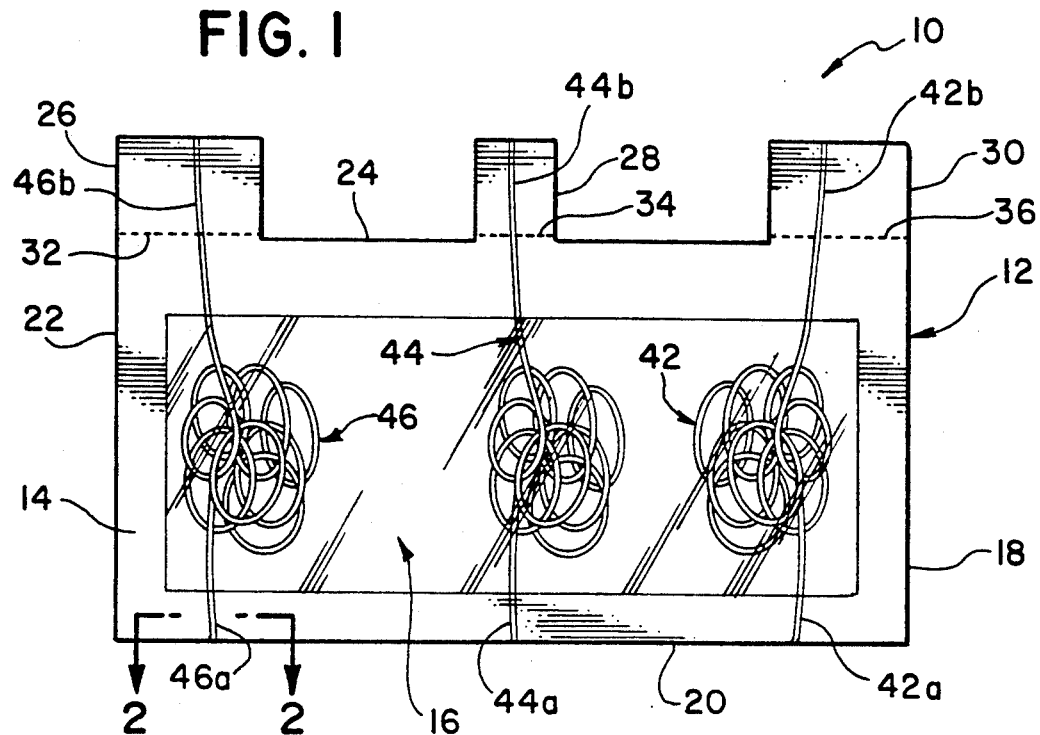

DENTAL HYGIENE APPARATUS

FIELD OF THE INVENTION

The present invention relates generally to dental hygiene products and, more particularly, a dental floss package in which a number of precut lengths of dental floss are packaged together and dispensed individually. A single package containing one or more dental floss segments has a pull-tab formed along the peripheral edge for each floss segment. One end of the floss is secured in the pull-tab and the other end is secured in the peripheral edge of the package. By tearing away each tab, a single filament of floss can be removed from the package without destroying the integrity of the entire package.

BACKGROUND OF THE INVENTION

Dental floss is typically sold in packages containing fifty yards or more of un-cut floss. The user dispenses as much as needed for a floss treatment, and then cuts the floss into a desirable length using a cutting edge provided within the package.

While the at least one aforementioned packaging and dispensing technique is well suited for most situations, there are times when it is preferable to use pre-cut and individually packaged dental floss segments, or packages containing a small number of pre-cut segments. For example, when traveling, it may be more convenient for the traveler to carry a supply of floss-segments corresponding to a length of stay. Moreover, as a convenience to the traveler, hotels and motels may wish to provide complimentary supplies of individually packaged (or packaged in small groups) dental floss segments.

My prior U.S. Pat. No. 4,693,365 discloses an apparatus and method for storing a plurality of filaments within a sealed package. An untangled and unknotted filament is stored within a flexible package, and is removed by tearing a portion of the package to expose the filament to the outside environment. The filaments are positioned such that the central portion of the filament is bunched within the package, while the first and second ends of the filament are securely held within the sealed edges of the package. When a user desires to remove a filament from the package, the sealed edge of the package is torn open and the floss may then be removed from the package. When the sealed edge is torn the tear line crosses the sealed enclosure and thus, the integrity of the package is compromised.

My prior U.S. Pat. No. Des. 289,973 discloses the design of a filament package containing two individual filaments or floss segments. Peripheral edge notches provide a tear-open capability and induce the formation of a tear line that crosses and thus compromises the sealed enclosure.

It has been known to provide therapeutic agents on dental floss, either as a coating or an impregnant. Examples can be found in U.S. Pat. Nos. 4,911,927 to Hill et al. (a floss containing chemotherapeutic preparations); 5,098,711 to Hill et al. (a floss containing cleaning solutions); and 5,165,913 to Hill et al. (silicone and chemotherapeutic agents). These agents have not been provided in individually packaged floss segments, however. U.S. Pat. No. 4,712,572 to Hovel discloses a tooth shaped package for storing a single piece of dental floss. The floss is securely packaged by permanently sealing the ends of the floss within the edges of the package. The floss is anchored within the sealed edges so that the package halves can be used as handles when the package is opened. The sealed enclosure defined by the package is severely compromised by tearing open the package, and clearly, the package could not be re-used for additional floss dispensing.

A continuing need exists for an improved dental hygiene apparatus capable of packaging one or more dental floss segments and dispensing same without compromising the sealed enclosure of the floss package.

SUMMARY OF THE INVENTION

The present invention avoids and overcomes these and other problems by facilitating the proper opening of filament containing packages. It is therefore an object of the instant invention to provide a dental hygiene apparatus which includes a closed package for storing a plurality of filaments, especially, dental floss, such that the integrity of the entire package is not destroyed when one of the filaments is removed.

Another object of the present invention is to provide a package which is inexpensive, simple in construction and easy to store and use.

These objects are achieved by providing a package containing at least one filament which can be removed without destroying the integrity of the entire package. End portions of the filament extend into and are entrapped within the sealed edges of the package. However, the end portions are only sealed within the sealed edges of the package to the extent that they can easily slide out of the sealed edges, leaving a small hole in the edge.

The material construction of the package determines the appropriate method of opening. For packages constructed from material that are easily tearable, only an indication of the proper opening position is necessary, such as by a physical tear line or other graphic representation. If desired, the indication could be accompanied by an imprinted message "tear here", to direct the user's attention as to the proper technique for opening the package. The tear line may be imprinted on both sides of the package to avoid any possible user error. Where the material of the package resists tearing, a perforated line, cut, or notch, is used to allow for easier and proper removal of the filament. Once again the opening location should preferably include an imprinted tear line and message as previously indicated. Additionally, a tab, containing an end of each filament extends from the package to facilitate tearing and opening of the package to extract the filament therefrom.

In use, the package is torn at an appropriate location and the filament is withdrawn from the package. Because the ends of the filament are not rigidly held within the sealed edges of the package, the filament slides through a small hole in the edge of the package. As the filament is withdrawn, the far end of the filament slides out of an edge of the package without destroying the integrity of the package. The removal of the far end of the filament leaves a small hole in the edge of the package. The filament is finally removed from the package, and leaves only a small hole in the edge of the package adjacent to the location where the package was torn to remove the filament.

Other objects and advantages, as well as a more complete understanding of the present invention, will appear from the following explanation of exemplary embodiments and the accompanying drawings.

BRIEF DESCRIPTION OF THE DRAWINGS

FIG. 1 is a side elevational view of a first embodiment of the instant invention;

FIG. 2 is a cross-sectional view, taken along line 2—2 of FIG. 1;

FIG. 3A is an enlarged, partial longitudinal cross-sectional view of a dental floss segment impregnated and/or coated with powder;

FIG. 3B is an enlarged, partial longitudinal cross-sectional view of a dental floss segment coated with wax;

FIG. 4 is a partial side elevation of the first embodiment showing the floss within the package and after the floss has been removed from the package;

FIG. 5 is a partial cross-sectional view, taken along line 5—5 of FIG. 4 after the floss has been removed;

DETAILED DESCRIPTION OF THE PREFERRED EMBODIMENT

Figure 6:
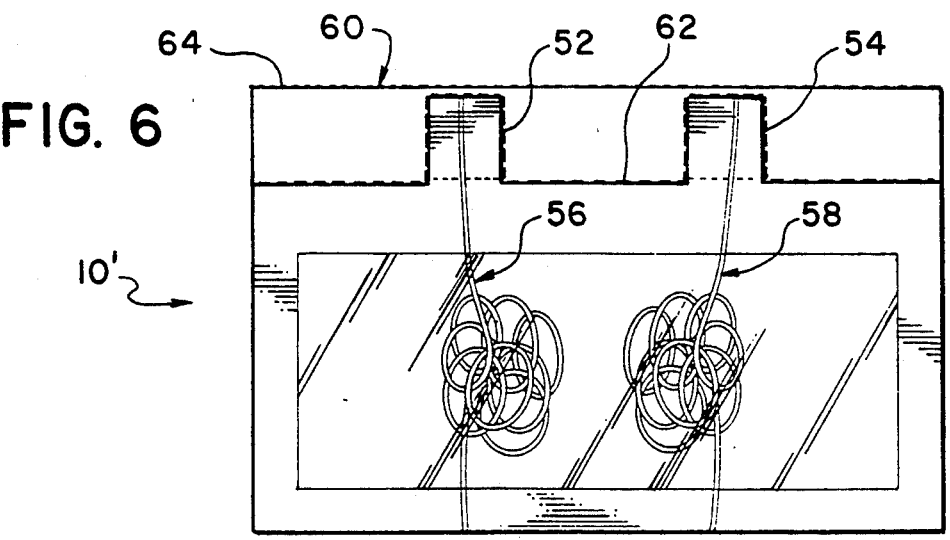
FIG. 6 shows a side elevational view of a second embodiment of the instant invention where a header is secured to the top edge of the package.

Referring to FIG. 1, a dental hygiene apparatus 10 includes a package 12 having a continuous sealing area 14 which defines a sealing enclosure 16. The package 12 has peripheral edges 18, 20, 22 and 24 which define a generally rectangular shape, although the package can be configured to include virtually any shape. In the embodiment of FIG. 1, the peripheral edge 24 has three integral pull-tabs 26, 28 and 30. Preferably, score lines 32, 34 and 36 are disposed in line with peripheral edge 24 such that when the pull-tabs are removed, the peripheral edge 24 is a straight line between the two peripheral edges 18 and 22. The score lines provide a frangible connection between the respective pull-tabs 26, 28 and 30 and the package 12.

The package 12 is formed by overlying two sheets 38 and 40, as seem in FIG. 2, and bonding the two sheets together. The bonding step forms the sealing area 14 in which the inner surfaces of the two sheets are bonded together. Generally, the process of making the package 12 can be realized by using the methodology and apparatuses described in the aforementioned U.S. Pat. No. 4,693,365, or other appropriate devices and methods.

Three dental floss segments 42, 44 and 46 are disposed in the sealed enclosure 16. During formation of the package 12, the opposite axial ends of each floss segment is placed between the two sheets 38 and 40 and then bonded there between. Ends 42a, 44a and 46a are bonded in the sealing area 14 along the peripheral edge 20. The opposite ends 42b, 44b and 46b are bonded in the tabs 30, 28 and 26, respectively. The medial portion of each dental floss segment 42, 44 and 46 is coiled for easy dispensing in rapid, un-knotted fashion.

As shown in FIG. 3A, the floss segments, such as segment 46, are coated, impregnated or otherwise treated with a powder 48, preferably having a tribological quality such that the floss segments can be pulled through the two sheets 38 and 40 without tearing the package. FIG. 3B is a view similar to FIG. 3A showing an alternative floss segment 46' with a wax coating 48'. A variety of therapeutic agents and/or tribological agents can be employed. In each case, the additive material has the effect of preventing adherence, or a firm connection from being made between the sheets 38 and 40 and the ends of the floss segments. Powders include "dental powder" (a type of cleaner) and baking soda.

As shown in FIG. 4, in order to remove floss segment 46 for a floss treatment, the pull-tab 26 is caused to tear along the score line 32, thus making the peripheral edge 24 continuous. As shown in FIG. 5, when the segment is pulled through the sealing area 14 a small hole 50 remains.

Referring to FIG. 6, an alternative embodiment of dental hygiene apparatus 10' has two pull-tabs 52 and 54 corresponding to two dental floss segments 56 and 58, respectively. A header 60 is provided on the peripheral edge 62 to protect the pull-tabs 52 and 54 during shipment, storage or transportation. When attached, the header 60 provides an outer peripheral edge 64. Detachment of the header 60 from the package 10' is facilitated by score lines provided on the peripheral edge 62. The score lines provide a frangible connection which is weaker than the frangible connection provided by the score lines between the pull-tabs 52 and 54 and the package 10'. In all other aspects, the embodiment of FIG. 6 is the same as the embodiment of FIG. 1. Likewise, any other embodiments described herein could be provided with a suitable header. During manufacture, the header 60 and pull-tabs 52 and 54 could be made in a simple stamping step after the package is formed by bonding the two opposed sheets together.

Figure 7:
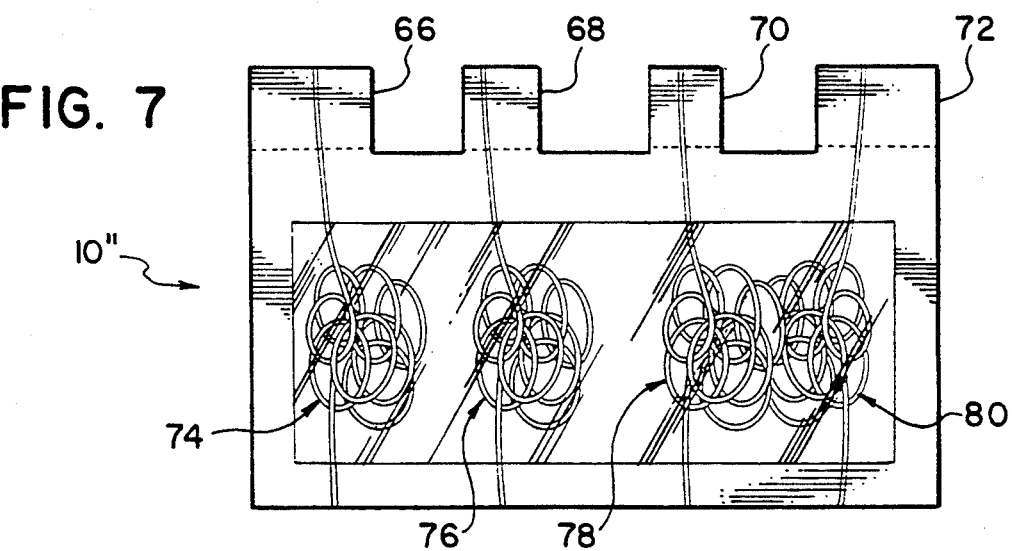
FIGS. 7 and 8 are side elevational views of alternate embodiments of the instant invention showing different numbers of pull-tabs and floss segments.
Figure 8:
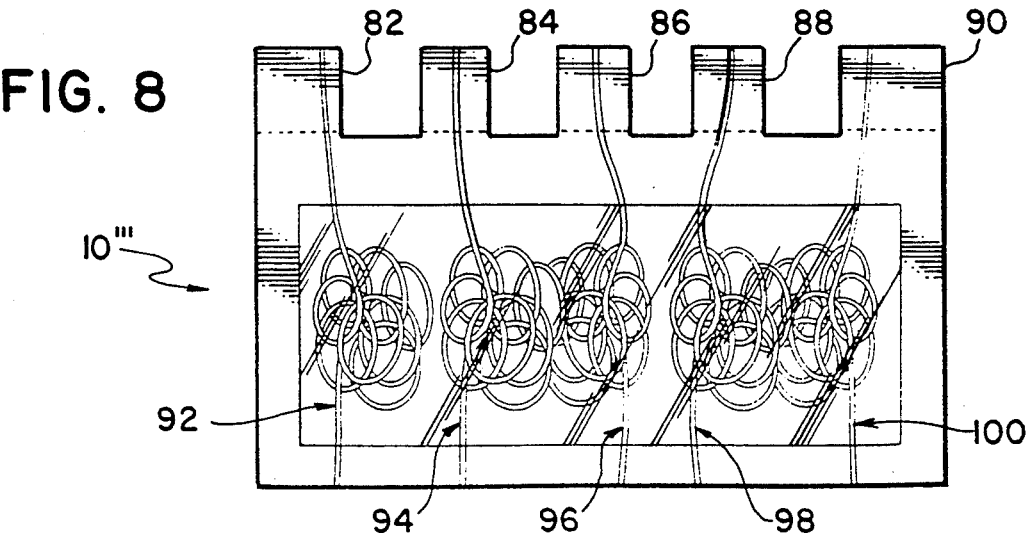

FIG. 7 is still another embodiment of a dental hygiene apparatus 10'' which includes four pull-tabs 66, 68, 70 and 72, each having an attached dental floss segment 74, 76, 78, and 80, respectively. FIG. 8 is another embodiment of a dental hygiene apparatus 10'' which includes five pull-tabs 82, 84, 86, 88 and 90, each having an attached dental floss segment 92, 94, 96, 98 and 100, respectively. The exact number of individual dental floss segments is a choice of practicality. The shape of the pull-tabs are preferably rectangular, as seen in the various embodiments, but other shapes may be employed. For example, for a particularly aesthetic and practical effect, the tabs can be formed in tooth-like shapes.

The packages described herein are made from conventional materials, which in the illustrated embodiments are substantially transparent. For example, a paper/polyethylene laminate may be used. Alternatively, polyester or polypropylene can be used if a tougher package material is desirable. Tougher material will necessitate the use of score lines, tear notches, or other suitable structures for initiating a tear line.

Once the pull-tab has been removed, the end of the floss segment within the pull-tab may immediately separate from the pull-tabs, or remain therein. Then, the user pulls either the exposed end of the segment outwardly, or the tab (still attached to the end) until the segment is removed. When the segment becomes taut, the lower end can be pulled from the lower peripheral edge sealing area. The wax coating and dental powder interfere with the sealed edges to prevent the formation of a tight seal where the first end and second end are located. As a result, openings are created and the dental floss is easily removed by sliding it through the openings. Once the dental floss is removed, only the small openings expose the open portion of the package.

Although the invention has been described with respect to the particular embodiments thereof, it should be realized that various changes and modifications may be made therein without departing from the spirit and scope of the invention.

What is claimed is:

1. A dental hygiene apparatus comprising:
a package having a peripheral edge and a continuous peripheral sealing area defining a sealed enclosure;
at least one integral pull-tab formed on the peripheral edge of the package; and
at least one filament segment disposed in the sealed enclosure of the package and having two opposite axial ends, one end being connected to the pull tab and the other end being connected to the package in the sealing area at a position spaced from the pull-tab;
said pull-tab being frangibly detachable from the package along a line spaced from the sealed enclosure, thus removing at least a substantial portion of the filament segment without substantially compromising the sealed enclosure when the pull-tab is detached.

2. A dental hygiene apparatus according to claim 1, wherein the at least one filament segment is a length of dental floss having a tribological agent coated thereon.

3. A dental hygiene apparatus according to claim 2, wherein the tribological agent is selected from the group consisting of wax, dental powder, and baking soda.

4. A dental hygiene apparatus according to claim 2, wherein the at least one filament segment is a length of dental floss having a therapeutic agent coated thereon.

5. A dental hygiene apparatus according to claim 1, further comprising a plurality of filament segments and a plurality of corresponding pull-tabs.

6. A dental hygiene apparatus according to claim 1, wherein the package comprises two rectangular sheets bonded together along the continuous peripheral sealing area to define four peripheral edge segments.

7. A dental hygiene apparatus according to claim 6, wherein the at least one pull-tab extends radially outward from and is integrally formed with the package at one of the four peripheral edge segments.

8. A dental hygiene apparatus according to claim 7, further comprising a score line formed between the package and the at least one pull-tab.

9. A dental hygiene apparatus according to claim 1, further comprising a score line formed between the package and the at least one pull-tab.

10. A dental hygiene apparatus according to claim 1, further comprising a header frangibly connected to the package and interfitting with the at least one pull-tab to define, when attached, a second, outer peripheral edge.

11. A method of packaging at least one filament segment having two opposite axial ends comprising the steps of:
forming a package having a peripheral edge, a continuous peripheral sealing area, and a sealed enclosure;
forming at least one pull-tab frangibly connected to the peripheral edge of the package; and
placing at least one filament segment in the sealed enclosure, during the package forming step, and detachably connecting one end of the filament segment to the at least one pull-tab and the opposite end to the package in the sealing area at a position spaced from the at least one tab;
the at least one pull tab being frangibly detachable from the package along a line spaced from the sealed enclosure.

12. A dental hygiene apparatus according to claim 11, wherein the at least one filament segment is a length of dental floss having a tribological agent coated thereon.

13. A dental hygiene apparatus according to claim 12, wherein the tribological agent is selected from the group consisting of wax, dental powder, and baking soda.

14. A dental hygiene apparatus according to claim 11, wherein the at least one filament segment is a length of dental floss having a therapeutic agent coated thereon.

15. A dental hygiene apparatus according to claim 11, further comprising a plurality of filament segments and a plurality of corresponding pull-tabs.

16. A dental hygiene apparatus according to claim 11, wherein the package comprises two rectangular sheets bonded together along the continuous peripheral sealing area to define four peripheral edge segments.

17. A dental hygiene apparatus according to claim 16, wherein the at least one pull-tab is integrally formed with the package at one of the four peripheral edge segments.

18. A dental hygiene apparatus according to claim 17, further comprising a score line formed between the package and the at least one pull-tab.

19. A dental hygiene apparatus according to claim 11, further comprising a score line formed between the package and the at least one pull-tab.

20. A dental hygiene apparatus according to claim 11, further comprising a header frangibly connected to the package and interfitting with the at least one pull-tab to define, when attached, a second, outer peripheral edge.

* * * * *